United States Patent [19]

Westman

[11] 4,377,381
[45] Mar. 22, 1983

[54] HOME CARE DENTURE CLEANING TOOL

[76] Inventor: Robert E. Westman, 61 Ninth St. S., Naples, Fla. 33940

[21] Appl. No.: 311,338

[22] Filed: Oct. 14, 1981

[51] Int. Cl.³ .............................................. A61C 3/00
[52] U.S. Cl. .................................. 433/141; 433/143; 433/144; 132/89; 132/75.4
[58] Field of Search ............... 433/142, 143, 144, 141; 128/304; 30/123.5, 142, 346, 356; 132/75.4, 89

[56] References Cited

U.S. PATENT DOCUMENTS

| | | | |
|---|---|---|---|
| D. 199,861 | 12/1964 | Eicher et al. | D44/29 |
| 945,713 | 1/1910 | Fritz | 433/144 |
| 1,410,296 | 3/1922 | Hannah | 433/144 |
| 1,503,610 | 8/1924 | Smith | 433/143 |
| 2,366,671 | 1/1945 | Montelius | 433/144 |
| 3,460,256 | 8/1969 | Fontana | 433/144 |
| 3,771,537 | 11/1973 | Schole | 433/142 |
| 4,060,897 | 12/1977 | Greenstein | 433/144 |
| 4,274,826 | 6/1981 | Huey et al. | 433/142 |

FOREIGN PATENT DOCUMENTS 836992  4/1952  Fed. Rep. of Germany ...... 433/141

*Primary Examiner*—John J. Wilson
*Attorney, Agent, or Firm*—Merrill N. Johnson

[57] ABSTRACT

The tool is designed for use by a denture wearer after the chemical cleaning of the denture or partial denture in the home. The tool is a double ended instrument with two blades mounted on opposite ends of an elongated handle, which handle preferably has a square cross-section and is made of plastic. One blade is spear-shaped and sharpened to a knife edge along its leading edges and at its apex. The second blade has a convex concave configuration and a rounded tip with all edges of this blade including its rounded tip sharpened to a knife edge.

6 Claims, 4 Drawing Figures

HOME CARE DENTURE CLEANING TOOL

BRIEF SUMMARY OF THE INVENTION

I have invented a unique tool for a novel purpose, namely, use by a denture wearer after the chemical cleaning of a denture or partial denture in the home.

After the denture has been soaked in a commercial denture cleaning solution or an ultrasonic cleaner, there often are bits of tartar, calculus or plaque or stains remaining which are usually located in areas of the denture difficult to reach. The contour and configuration of my tool are designed to physically clean these areas without damage to the denture.

My unique tool is a double ended instrument with two blades mounted on opposite ends of an elongated handle, which preferably has a square cross-section and is made of a suitable plastic such as styrene. One of the blades is spear-shaped and sharpened to a knife edge along its leading edges and at its apex or point. The second blade has a convex concave configuration with a smoothly rounded tip or end and all edges of this blade including its rounded tip are sharpened to a knife edge. Both blades are preferably made of high quality stainless steel.

Double ended tools for cleaning, repairing or adjusting teeth in the mouth for use by dentists and technicians are well known. Examples of such tools are shown in U.S. Pat. Nos. 1,003,213; 1,356,372; 1,397,395; 1,503,610; 2,677,843, and 3,985,147. However, none of these patents relate to tools for cleaning dentures or for use by denture wearers, and I am not aware of such a tool being marketed during my practice of dentistry for more than twenty years.

Instead, denture wearers dissatisfied with the appearance or condition of their dentures have had to resort to such makeshift devices as fingernail files, hairpins, kitchen knives and toothpicks, which result not only in poorly cleaned dentures by also damaged, ill fitting dentures and cut and punctured fingers.

My tool is scientifically designed for use by a nonprofessional denture wearer to safely and quickly remove tartar, calculus, plaque and stains from all areas of his denture without damaging the denture.

The spear-shaped blade is designed to fit into the interproximal spaces between the teeth of the denture. The apex or sharpened tip of this blade fits into even deep crevices of the interproximal areas and will dislodge material which has deposited there. The sides of the spear-shaped blade will remove debris or stains adhering to the buccal and lingual cervical areas of the teeth.

The convex concave blade is designed especially to remove material which has deposited onto the buccal and lingual flanges and palatal areas of the denture. This blade is also designed to remove unwanted deposits from the buccal, lingual and palatal areas of the ridge or tissue surfaces of the denture without removing or damaging these portions of the denture itself.

The regular use of my cleaning tool following the chemical cleaning of the denture or partial denture in the home by denture wearers will result in cleaner, better appearing dentures without resort to professional assistance to the denture wearer.

DETAILED DESCRIPTION

Figure 1:
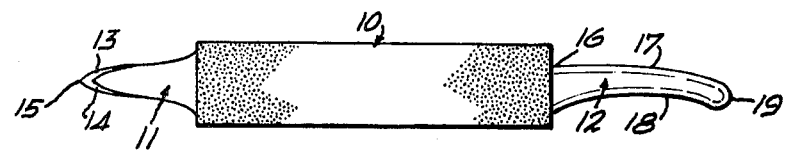
FIG. 1 is a side elevation of my denture cleaning tool.
Figure 2:
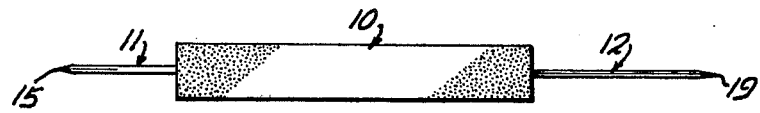
FIG. 2 is a side elevation of the tool shown in FIG. 1 turned through an angle of ninety degrees.

Referring to the drawing in which similar numerals represent corresponding parts in each of the four views, my denture cleaning tool comprises a handle 10 to which are secured two blades 11 and 12. The handle is elongated with a blade secured to each end and is preferably square in cross-section to permit it to be firmly grasped by the user. Handle 10 is preferably made of a hard plastic such as styrene or methyl methacrylate but may be metal, wood or bone.

Blades 11 and 12 are made preferably of a high quality stainless steel that can be sharpened and will retain a knife edge. Blade 11 is spear-shaped and sharpened to a knife edge along its leading edges 13 and 14 and apex 15. Blade 12 is straight at its shank 16 but with a concave convex configuration along its edges 17 and 18 ending in a smoothly rounded or arcuate tip 19. Edges 17 and 18 and also tip 19 are all honed to a knife edge.

The preferred embodiment of my denture cleaning tool that is shown in the drawing has an overall length of 4½ inches, measured from apex 15 of blade 11 to the tip 19 of blade 12. Blade 11 extends ¾ of an inch from the end of handle 10 to its apex 15. Blade 12 extends 1½ inches from the end of handle 10 to its rounded tip 19. Handle 10 is 2⅜ inches long and has a rectanglular cross-section of ⅜ by 7/16 inches.

Both blades 11 and 12 are made of flat tempered stainless steel stock approximately 0.05 inches in thickness, with the shank of each blade as it is set into handle 10 being ¼ inch in width.

For about one-half inch of its length, measured from the end of handle 10, the two edges of blade 11 are unsharpened and taper inwardly until blade 11 is ⅛ of an inch in width. Then blade 11 proceeds to form an equilateral triangle with edges 13 and 14 honed on both sides of the blade to a knife edge, thus providing apex 15 with a very sharp point. Leading edges 13 and 14 are each approximately ⅛ inch in length.

The shank 16 of blade 12 has a width of about ¼ inch but as its edges 17 and 18 curve in concave convex configuration, as best shown in FIG. 1 of the drawing, blade 12 becomes about 3/16 of an inch in width. Arcuate tip 19 is a semi-circle having a diameter of 3/16 of an inch. Edges 17 and 18 and tip 19 are honed on both sides of the blade to knifelike sharpness.

In use, the tool is grasped firmly in the hand of the denture user after having first cleaned the denture in a bath of conventional cleaning solution. Oral inspection of the denture or partial denture will often reveal deposits of tartar, calculus or plaque and stains in areas of the denture which are not easy to reach.

Figure 3:
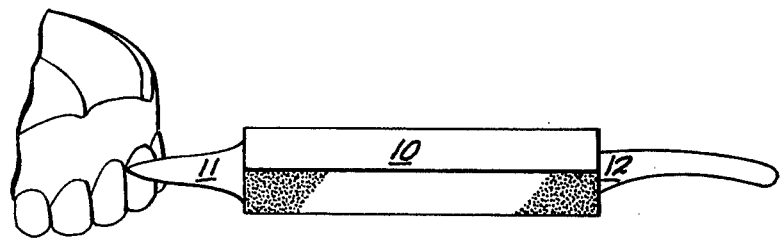
FIG. 3 is a side view of the spear-shaped blade of my tool being used to clean the interproximal space between the teeth of a denture.

As best shown in FIG. 3, pointed blade 11 is best used to remove materials deposited or lodged in the spaces between teeth or between a tooth and the gum.

Figure 4:
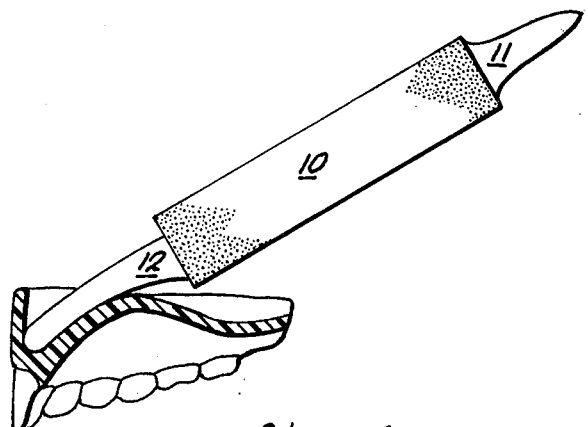
FIG. 4 is a side view of the concave convex blade of my tool being used to remove deposited material from the palatal area of the denture.

And as best shown in FIG. 4, curved blade 12 is best used to scrape unwanted stains and deposits from the buccal and lingual flanges and palatal areas of the denture. However, blade 12 is also designed to remove undesired material on the buccal, lingual and palatal areas of the ridge or tissue surfaces of the denture.

Both blades 11 and 12 have been designed and tested and are made of material which, when properly used, will not damage the areas and surfaces of the denture on which they are used. Thus the denture user can maintain his or her denture in a cleaner, better appearing condition without the need of professional assistance.

A preferred embodiment of my invention has been shown and described. However, modifications can be made without departing from the spirit and scope of my invention and it is intended that the invention be limited only by the scope of the following claims.

I claim:

1. A denture cleaning tool for use by denture wearers comprising:
    an elongated handle to be held in the hand of a user,
    a first generally flat blade secured to one end of the elongated handle for cleaning interproximal spaces and cervical areas of teeth on a denture,
    said first blade having a sharp pointed apex and two edges leading to said apex forming an angle of approximately 60° and the two edges leading to said apex being sharpened to a knife edge, and
    a second generally flat blade secured to the opposite end of said handle for cleaning flanges and palatal areas on a denture,
    said second blade having a concave convex configuration and a semicircular forward tip, the two edges and tip of said second blade being sharpened to a knife edge.

2. A denture cleaning tool according to claim 1, in which the overall length of the tool is approximately 4½ inches, the first blade is ¾ of an inch long, and the second blade is 1½ inches long.

3. A denture cleaning tool according to claim 1 or 2, in which the semicircular forward tip of the second blade has a diameter of approximatley 3/16 of an inch.

4. A denture cleaning tool according to claim 1 in which the two leading edges of the first blade and the two edges and tip of the second blade are honed to knife edge sharpness from both sides of the blade.

5. A denture cleaning tool according to claim 1 in which both blades are made from flat stainless steel stock having a thickness of 0.05 inches.

6. A denture cleaning tool according to claim 1 in which the elongated handle has a rectangular cross-section approximately ⅝ by 7/16 inches and is made of thermoplastic material.

* * * * *